(12) United States Patent
Kim

(10) Patent No.: US 10,733,268 B2
(45) Date of Patent: Aug. 4, 2020

(54) SELF-DIAGNOSIS APPARATUS FOR HEALTH TESTER AND SELF-DIAGNOSIS METHOD FOR HEALTH TESTER

(71) Applicant: OSANG HEALTHCARE CO., LTD., Anyang-si, Gyeonggi-do (KR)

(72) Inventor: Keun Young Kim, Seoul (KR)

(73) Assignee: OSANG HEALTHCARE CO., LTD., Anyang-si, Gyeonggi-Do (KR)

( * ) Notice: Subject to any disclaimer, the term of this patent is extended or adjusted under 35 U.S.C. 154(b) by 351 days.

(21) Appl. No.: 15/792,499

(22) Filed: Oct. 24, 2017

(65) Prior Publication Data

US 2018/0113989 A1 Apr. 26, 2018

(30) Foreign Application Priority Data

Oct. 24, 2016 (KR) .......................... 10-2016-0138682

(51) Int. Cl.
*G06F 11/30* (2006.01)
*G01N 33/49* (2006.01)
(Continued)

(52) U.S. Cl.
CPC ... *G06F 19/3418* (2013.01); *G01N 33/48792* (2013.01); *G01N 33/49* (2013.01);
(Continued)

(58) Field of Classification Search
CPC .............. G01N 33/48792; G01N 33/49; G06F 19/3418; G16H 10/40; G16H 40/40; G16H 40/63; H04L 67/12; A61B 5/14532
(Continued)

(56) References Cited

U.S. PATENT DOCUMENTS

| 6,219,626 B1 * | 4/2001 | Steinmetz | ........... G06F 11/2257 |
| | | | 702/182 |
| 2004/0015102 A1 * | 1/2004 | Cummings | .......... A61B 5/7475 |
| | | | 600/584 |
| 2008/0294024 A1 * | 11/2008 | Cosentino | .......... A61B 5/14532 |
| | | | 600/309 |

FOREIGN PATENT DOCUMENTS

| KR | 10-0196537 | 6/1999 |
| KR | 10-1367262 | 2/2014 |

(Continued)

OTHER PUBLICATIONS

Kim, et al., "Study of Chronic Diseases Management System Using LPWAN," INFOPIA Co., Ltd., Jun. 22, 2016, 5 pages (English Abstract).
Kim, et al., "Research on Improving Medication Adherence With the Wearable Device," Infopia Co., Ltd., Jun. 29, 2016, 4 pages.
(Continued)

*Primary Examiner* — John H Le
(74) *Attorney, Agent, or Firm* — Lewis Roca Rothgerber Christie LLP

(57) ABSTRACT

The present invention relates to a self-diagnosis apparatus for a health tester and a self-diagnosis method for a health tester. For a health tester that displays health diagnostic information of a user obtained using a strip and has a communication function capable of transmitting the diagnostic information to an external device, the self-diagnosis apparatus includes: a virtual strip unit mounted inside of the health tester and configured to include one or more virtual
(Continued)

strips in which predetermined specific data is measured; a virtual strip selector configured to select at least one virtual strip from the one or more virtual strips through switching; and a diagnosis and determination unit configured to a measurer and diagnose a status or an occurrence of a failure of the health tester.

10 Claims, 6 Drawing Sheets

(51) Int. Cl.
  G01N 33/487    (2006.01)
  G06F 19/00     (2018.01)
  G16H 10/40     (2018.01)
  G16H 40/63     (2018.01)
  G16H 40/40     (2018.01)
  H04L 29/08     (2006.01)
(52) U.S. Cl.
  CPC .............. *G16H 10/40* (2018.01); *G16H 40/40* (2018.01); *G16H 40/63* (2018.01); *H04L 67/12* (2013.01)

(58) Field of Classification Search
  USPC ..... 702/19, 57, 62, 119, 120, 182, 183, 185; 600/309, 584
  See application file for complete search history.

(56) References Cited

FOREIGN PATENT DOCUMENTS

KR    2016-0099942      8/2016
KR    2016-0102232 A    8/2016

OTHER PUBLICATIONS

Keun Young Kim, et al., Thesis: "Study of Chronic Diseases Management System Using LPWAN," Infopia Co., Ltd., Jun. 22, 2016, 5 pages.

Keun Young Kim et al., Thesis: "Research on Improving Medication Adherence With the Wearable Device," Infopia Co., Ltd. Jun. 29, 2016, 4 pages.

Report entitled, "The Development of the Personal Health Record Based Smart Medication Management System," Aug. 15, 2016, 107 pages.

Office action issued in corresponding Korean Patent Application No. 10-2016-0138682, dated Nov. 20, 2017, 8 pages.

* cited by examiner

SELF-DIAGNOSIS APPARATUS FOR HEALTH TESTER AND SELF-DIAGNOSIS METHOD FOR HEALTH TESTER

CROSS-REFERENCE TO RELATED APPLICATION

This application claims priority to and the benefit of Korean Patent Application No. 10-2016-0138682, filed on Oct. 24, 2016, the disclosure of which is incorporated herein by reference in its entirety.

BACKGROUND

1. Field of the Invention

The present invention relates to a self-diagnosis apparatus for a health tester and a self-diagnosis method for a health tester, and more particularly, to a self-diagnosis apparatus for a health tester and a self-diagnosis method for a health tester which enable a health tester to autonomously diagnose a performance or failure thereof, thereby ensuring reliability of diagnostic data.

2. Discussion of Related Art

As interest in point of care (POC) devices has recently increased, the development of related devices is also increasing.

As a representative example of such devices, there is a health tester which diagnoses an infection or disease using blood or a bodily fluid. When a drop of blood is dropped on a strip-shaped test paper inserted into the health tester, depending on the type of test paper, dozens of diseases, such as diabetes, hyperlipidemia, and a myocardial infarction, may be identified and a health status of a user may be checked.

The measured information is automatically transmitted to a smartphone or server and sent to a doctor for further diagnosis and consultation.

However, despite the health tester's convenience in use, since it is not easy for the health tester to perform performance verification and failure diagnosis, reliability of data cannot be guaranteed.

For example, in order to check the performance of the health tester, there is only a method of periodically comparing blood diagnostic results from a hospital with blood diagnostic data obtained using the health tester and verifying performance of the health tester on the basis of whether the two pieces of data match.

Hence, there is a demand for a method which enables a user to more conveniently and easily verify performance of the health tester itself and enables automatic diagnosis of a failure thereof, thereby ensuring the reliability of diagnostic data.

A prior art of the present invention is disclosed in Korean Patent Registration No. 10-1367262 (registered on Feb. 19, 2014, titled "Blood Glucose Sensor and Sensing Error Detecting Method Using the Same")

SUMMARY OF THE INVENTION

According to one aspect of the present invention, the present invention is devised to solve the above-described problems, and an objective of the present invention is to provide a self-diagnosis apparatus for a health tester and a self-diagnosis method for a health tester which enable a health tester to autonomously diagnose a performance or failure thereof, thereby ensuring reliability of diagnostic data.

In one general aspect, there is provided a self-diagnosis apparatus for a health tester configured to display health diagnostic information of a user obtained using a strip and have a communication function capable of transmitting the diagnostic information to an external device, the self-diagnosis apparatus including: a virtual strip unit mounted inside of the health tester and configured to include one or more virtual strips in which predetermined specific data is measured; a virtual strip selector configured to select at least one virtual strip from the one or more virtual strips through switching; and a diagnosis and determination unit configured to connect the selected at least one virtual strip selected by the virtual strip selector to a measurer and diagnose a status or an occurrence of a failure of the health tester on the basis of diagnostic data of the virtual strip measured by the measurer when the status or the occurrence of a failure of the health tester is self-diagnosed.

The diagnosis and determination unit may sequentially connect all of the virtual strips of the virtual strip unit to the measurer, or simultaneously select one or more of the virtual strips and connect the selected virtual strips to the measurer to self-diagnose the status or the occurrence of a failure of the health tester.

The diagnosis and determination unit may perform at least one of a current or voltage analysis, an impedance analysis, an impulse analysis, and a spectrum analysis to diagnose the status or the occurrence of a failure of the health tester.

The one or more virtual strips may be each configured as a strip equivalent circuit in which the predetermined specific data is measured.

The virtual strip selector may measure and diagnose an actual strip at a time of actual blood diagnosis and measure and diagnose the virtual strip at a time of self-diagnosis under control of the diagnosis and determination unit.

The virtual strip selector and the virtual strip unit may be implemented as one component or module, and the virtual strip unit may be implemented to be detachable.

The diagnosis and determination unit may compare the diagnostic data of the at least one virtual strip and diagnostic data for each of the virtual strips stored in advance in an internal memory and diagnose the status of the health tester according to whether the two pieces of data match each other within an error range.

The virtual strip is implemented as an equivalent electronic circuit corresponding to a function of an actual strip on which any blood is collected.

The virtual strip may include a transistor operating as a switch, wherein when a control signal output from the controller is applied to a gate of the transistor, a source and a drain are connected to each other and an RLC equivalent circuit is connected to the measurer.

The virtual strip may be implemented such that a value of the RLC equivalent circuit is set differently according to a type of virtual strips for self-diagnosis of different operations of the health tester, and accordingly, the measurer measures different diagnostic data depending on the type of virtual strip.

When the status of the health tester does not meet a reference condition or a failure occurs, the diagnosis and determination unit may display the status and set the health tester to be unavailable for use or measurement.

In another general aspect, there is provided a self-diagnosis method for a health tester, the self-diagnosis method including: detecting, by a diagnosis or determination unit, whether a health tester is powered on or whether a specific button provided on the health tester is pressed; sequentially or simultaneously selecting and diagnosing, by the diagnosis and determination unit, at least one virtual strip of a virtual strip unit in a self-diagnosis mode; and diagnosing, by the diagnosis and determination unit, a status of the health tester on the basis of diagnostic data of the selected at least one virtual strip, and outputting a diagnostic result.

The diagnosis and determination unit may diagnose blood using an actual strip in an actual strip diagnosis mode and self-diagnose a performance or failure of the health tester itself in the self-diagnosis mode.

In the diagnosing of the status of the health diagnosis device, the diagnosis and determination unit may compare the diagnostic data of the at least one virtual strip and diagnostic data for each of the virtual strips stored in advance in an internal memory and diagnose the status of the health tester according to whether the two pieces of data match each other within an error range.

In still another general aspect, there is provided a self-diagnosis method for a health tester, the self-diagnosis method including: detecting, by a diagnosis or determination unit, whether a health tester is power on or whether a specific button provided on the health tester is pressed; sequentially or simultaneously selecting and diagnosing, by the diagnosis and determination unit, at least one virtual strip of a virtual strip unit in a self-diagnosis mode; transmitting, by a controller, diagnostic data of the selected at least one virtual strip to a server through the Internet; and diagnosing, by the server, a status of the health tester on the basis of the diagnostic data of the selected at least one virtual strip received through the Internet, and receiving, by the diagnosis and determination unit, a diagnostic result from the server through a communicator and outputting the diagnostic result.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
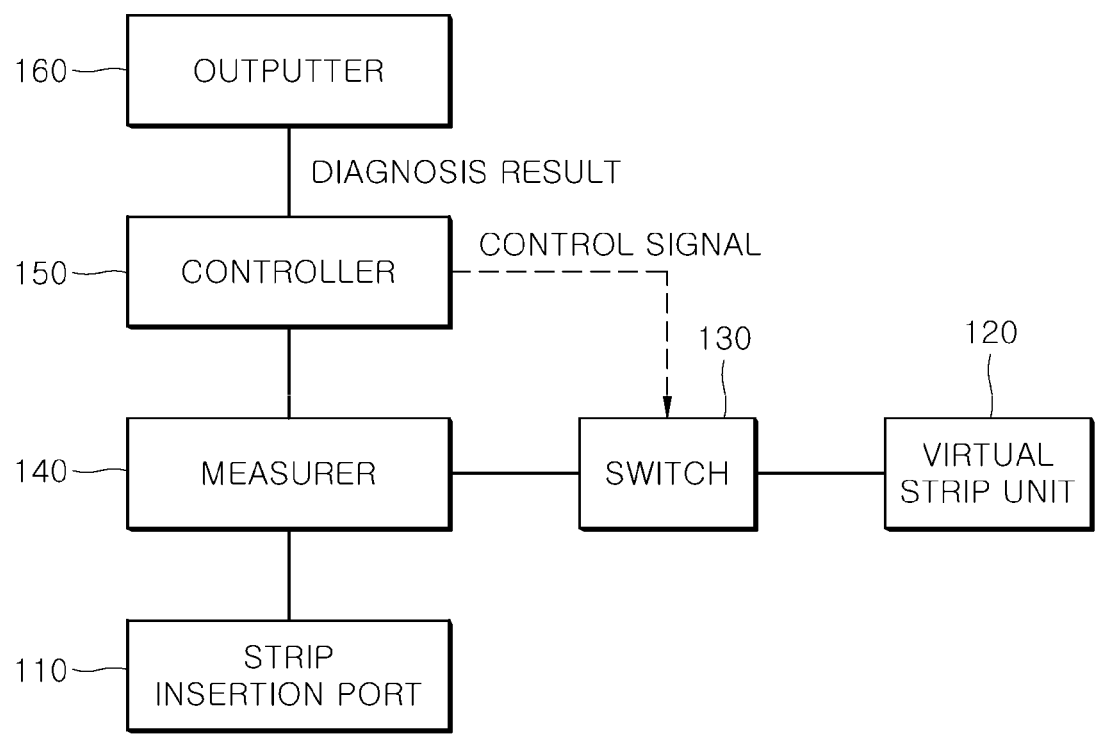
FIG. 1 is an exemplary diagram illustrating a schematic configuration of a self-diagnosis apparatus for a health tester according to one embodiment of the present invention.

Hereinafter, embodiments of a self-diagnosis apparatus for a health tester and a self-diagnosis method for a health tester according to the present invention will be described with reference to the accompanying drawings.

Thickness of lines and sizes of constituent elements illustrated in the drawings may be exaggerated for the purpose of clarity and convenience of description. In addition, some terms described below are defined in consideration of functions in the present invention, and meanings thereof may vary depending on, for example, a user or operator's intention or custom. Therefore, the meanings of terms should be interpreted on the basis of the scope throughout this specification.

Figure 2:
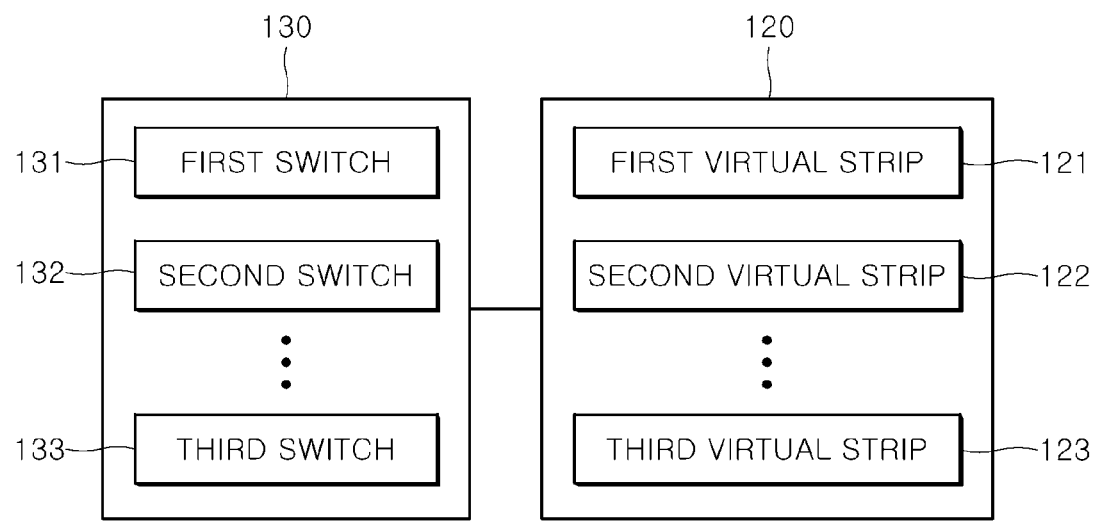
FIG. 2 is an exemplary diagram illustrating a virtual strip in FIG. 1 in detail.
Figure 3:
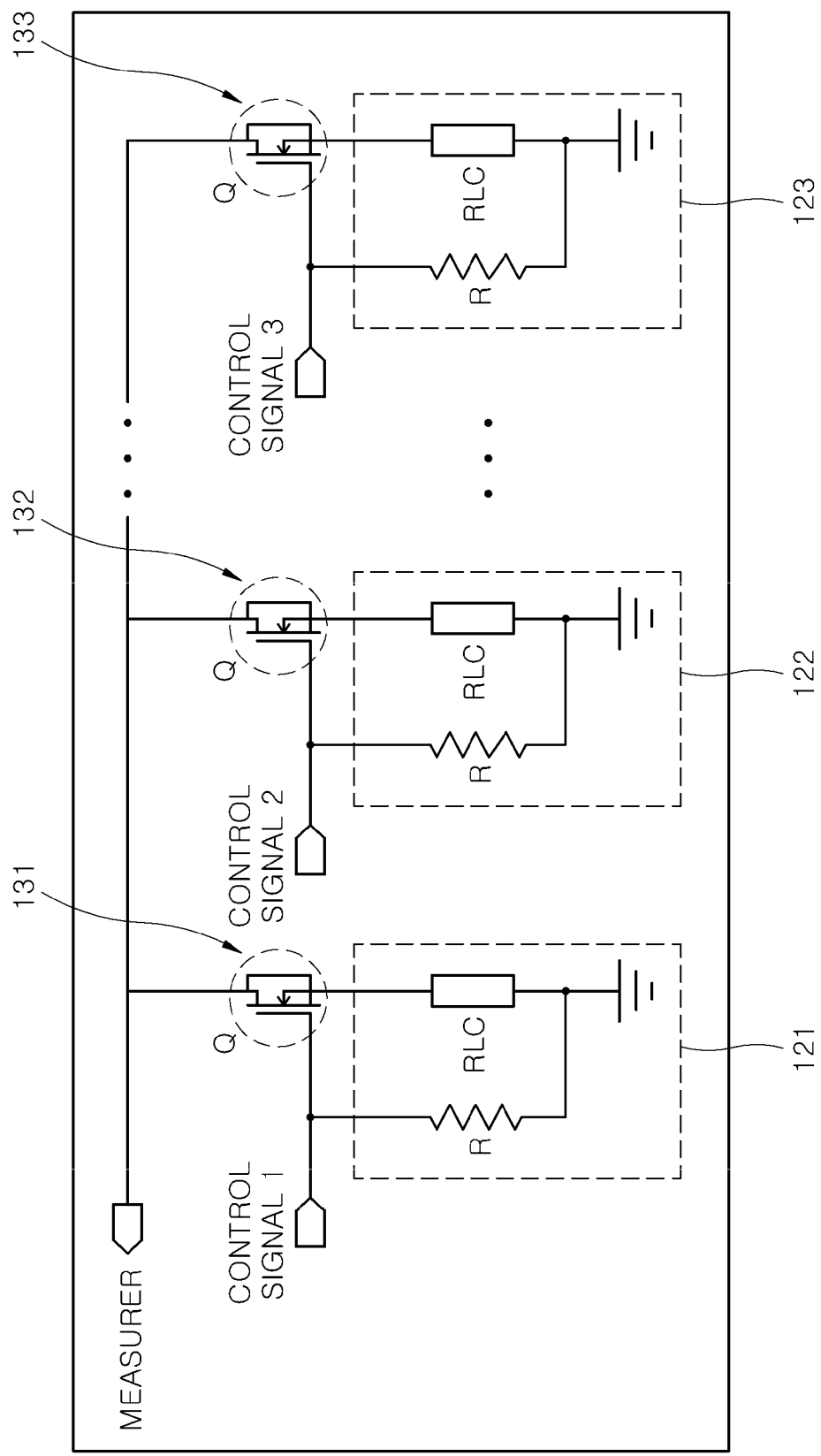
FIG. 3 is an exemplary diagram illustrating an equivalent circuit of the virtual strip in FIG. 2.

FIG. 1 is an exemplary diagram illustrating a schematic configuration of a self-diagnosis apparatus for a health tester according to one embodiment of the present invention, FIG. 2 is an exemplary diagram illustrating a virtual strip in FIG. 1 in detail, and FIG. 3 is an exemplary diagram illustrating an equivalent circuit of the virtual strip in FIG. 2.

As shown in FIG. 1, the self-diagnosis apparatus for a health tester includes a strip insertion port 110, a virtual strip unit 120, a switch 130, a measurer 140, a controller 150, and an outputter 160.

An actual test paper (or a strip) for collecting actual blood to be diagnosed by a health tester is inserted into the strip insertion port 110.

The virtual strip unit 120 is a virtual strip which is included in the health tester and is configured to measure (or diagnose) predetermined specific data.

The virtual strip unit 120 includes one or more virtual strips 121, 122, and 123, as shown in FIG. 2.

Each of the one or more virtual strips 121 to 123 is configured as an equivalent circuit in which the predetermined specific data is measured (or diagnosed), as shown in FIG. 3.

The switch 130 switches one or more virtual strips to be selected as targets to be measured by the measurer 140 among the one or more virtual strips of the virtual strip unit 120. Therefore, in the present embodiment, the switch 130 may be referred to as a virtual strip selector.

For example, the switch 130 switches the virtual strip unit 120 and the measurer 140 such that the virtual strip unit 120 and the measurer 140 are connected to each other at a time of self-diagnosis of a status (or an occurrence of a failure) of the health tester.

In the present embodiment, for convenience of description, the switch 130 and the virtual strip unit 120 are illustrated as separate components (or modules). However, in an actual implementation, the switch 130 and the virtual strip unit 120 may be implemented as a single component (or module). In addition, the virtual strip unit 120 may be implemented to be detachable as needed (or depending on a product).

The measurer 140 diagnoses at least one of the virtual strips 121 to 123 of the virtual strip unit 120 connected through the switch 130.

At this time, the measurer 140 may sequentially diagnose all of the virtual strips 121 to 123 of the virtual strip unit 120 according to a predetermined order, or may simultaneously select and diagnose one or more of the virtual strips 121 to 123.

When the status (or the occurrence of a failure) of the health tester is self-diagnosed, the controller 150 controls the switch 130 according to a pre-set program to sequentially connect all of the strips 121 to 123 of the virtual strip unit 120 to the measurer 140 according to a predetermined order, or to simultaneously select and connect one or more of the virtual strips 121 to 123 to the measurer 140.

In addition, the controller 150 compares diagnostic data of at least one virtual strip measured by the measurer 140 and predetermined specific data (e.g., diagnostic data for each strip stored in advance in an internal memory) for the virtual strip. When the two pieces of data (i.e., the diagnostic data and the diagnosis data stored in the internal memory) match each other within an error range, the controller 150 may diagnose that the health tester is in a normal state. Thus, in the present embodiment, the controller 150 may be referred to as a diagnosis and determination unit.

The outputter 160 outputs a diagnostic result obtained by the controller 150.

Referring to FIG. 2, the virtual strip unit 120 includes the one or more virtual strips 121 to 123.

For example, since the health tester can diagnose dozens of diseases, such as diabetes, hyperlipidemia, and myocardial infarction, according to the type of test paper (i.e., strip), the health tester may include a number of virtual strips corresponding to the number of diagnosable health statuses such that the health tester can test for each of the diagnosable health statuses.

Therefore, the switch 130 may include one or more switches 131, 132, and 133. However, the switches 131 to 133 do not need to correspond to the virtual strips in one-to-one correspondence, and one or more virtual strips may be selected by a combination of the switches 131 to 133.

Meanwhile, each of the virtual strips 121 to 123 of the virtual strip unit 120 may be implemented as an equivalent circuit (i.e., an electronic circuit corresponding to a function of an actual strip on which blood or a bodily fluid is collected), as shown in FIG. 3.

Referring to FIG. 3, the virtual strips 121 to 123 and the switches 131 to 133 are configured such that, when control signals (control signals 1 to 3) output from the controller 150 are applied to gates of transistors (or FET transistors) Q operating as switches, sources and drains are connected to each other and RLC equivalent circuits RLC are connected to the measurer 140.

In this case, a value of the RLC equivalent circuit RLC is set differently according to the type of virtual strip, and accordingly, the measurer 140 measures different diagnostic (or measurement) data depending on the type of virtual strip.

For example, when it is assumed that a value (i.e., diagnostic data) (e.g., impedance, response current, etc.) obtained by measuring the first virtual strip 121 is A, a value (i.e., diagnostic data) obtained by measuring the second virtual strip 122 is B, and a value obtained by measuring the third virtual strip 123 is C, the controller 150 may measure the first virtual strip 121 by turning on only the first switch 131, measure the second virtual strip 122 by turning on only the second switch 132, measure the third virtual strip 123 by turning on only the third switch 133, and then may determine an occurrence of a failure (or a status) by taking into consideration a range of each value (diagnostic data), overall linearity, and statistical characteristics thereof (i.e., by comparing each of the values with a kind of reference value for each virtual strip stored in the internal memory).

Alternatively, the controller 150 may measure diagnostic (or measurement) data by selectively combining and turning on one or more of the switches 131 to 133.

In addition, when the status of the health tester does not meet a reference condition or a failure occurs, the control unit 150 may display the status through the outputter 160 and may set (or control) the health tester to be unavailable for use or measurement.

Figure 4:
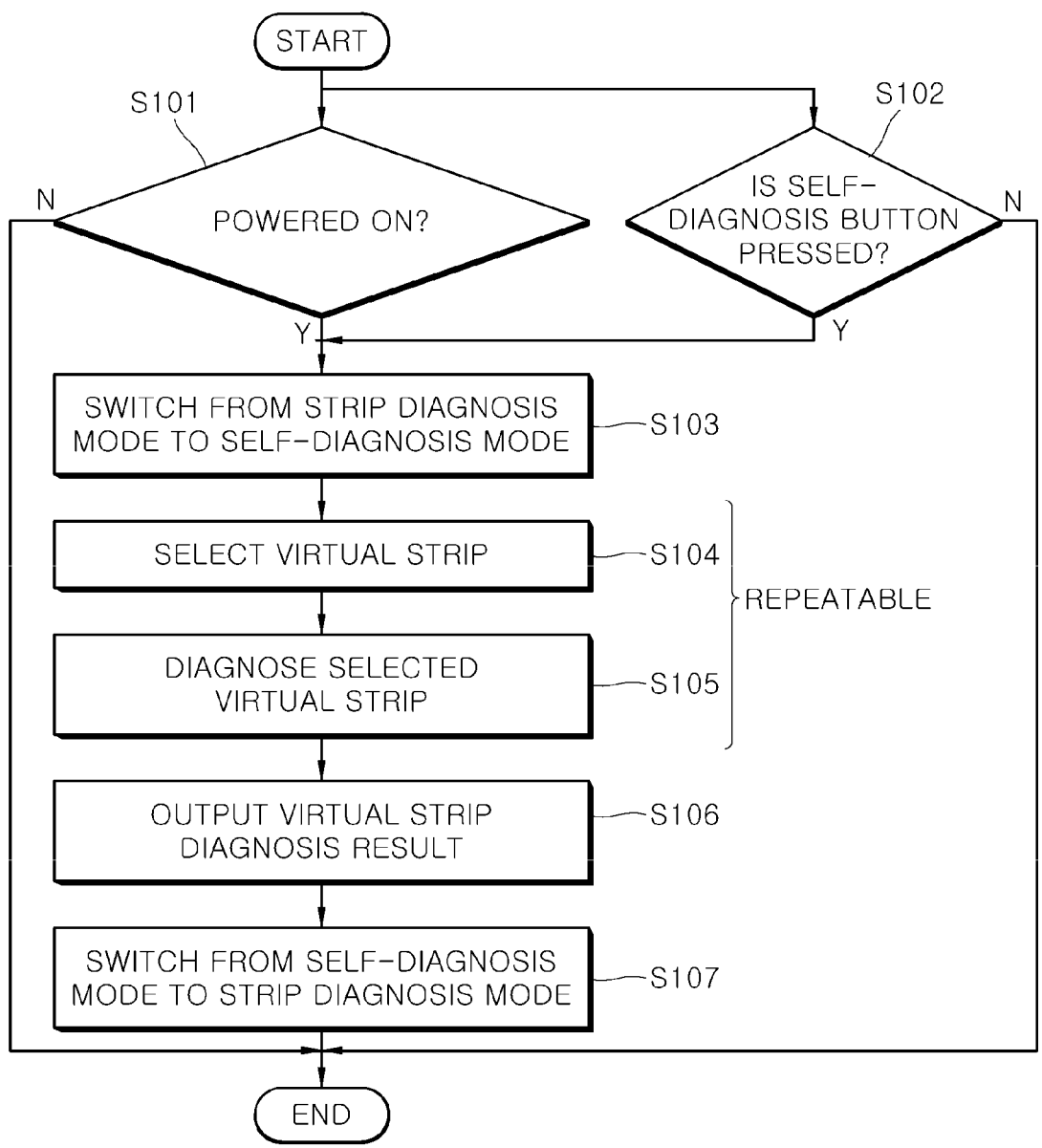
FIG. 4 is a flowchart illustrating a self-diagnosis method for a health tester according to a first embodiment of the present invention.
Figure 5:
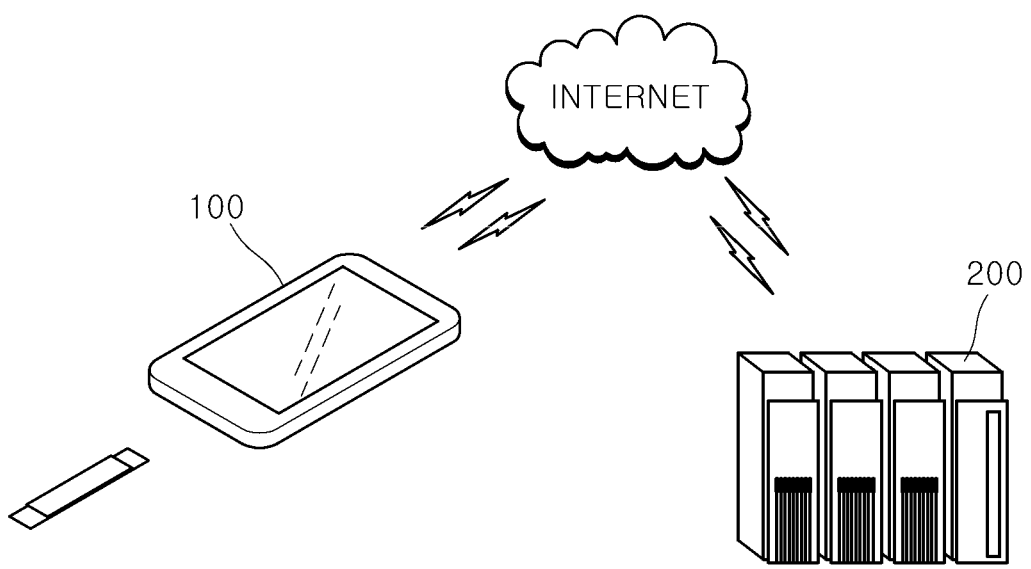
FIG. 5 is an exemplary diagram for describing a self-diagnosis method for a health tester according to a second embodiment of the present invention.
Figure 6:
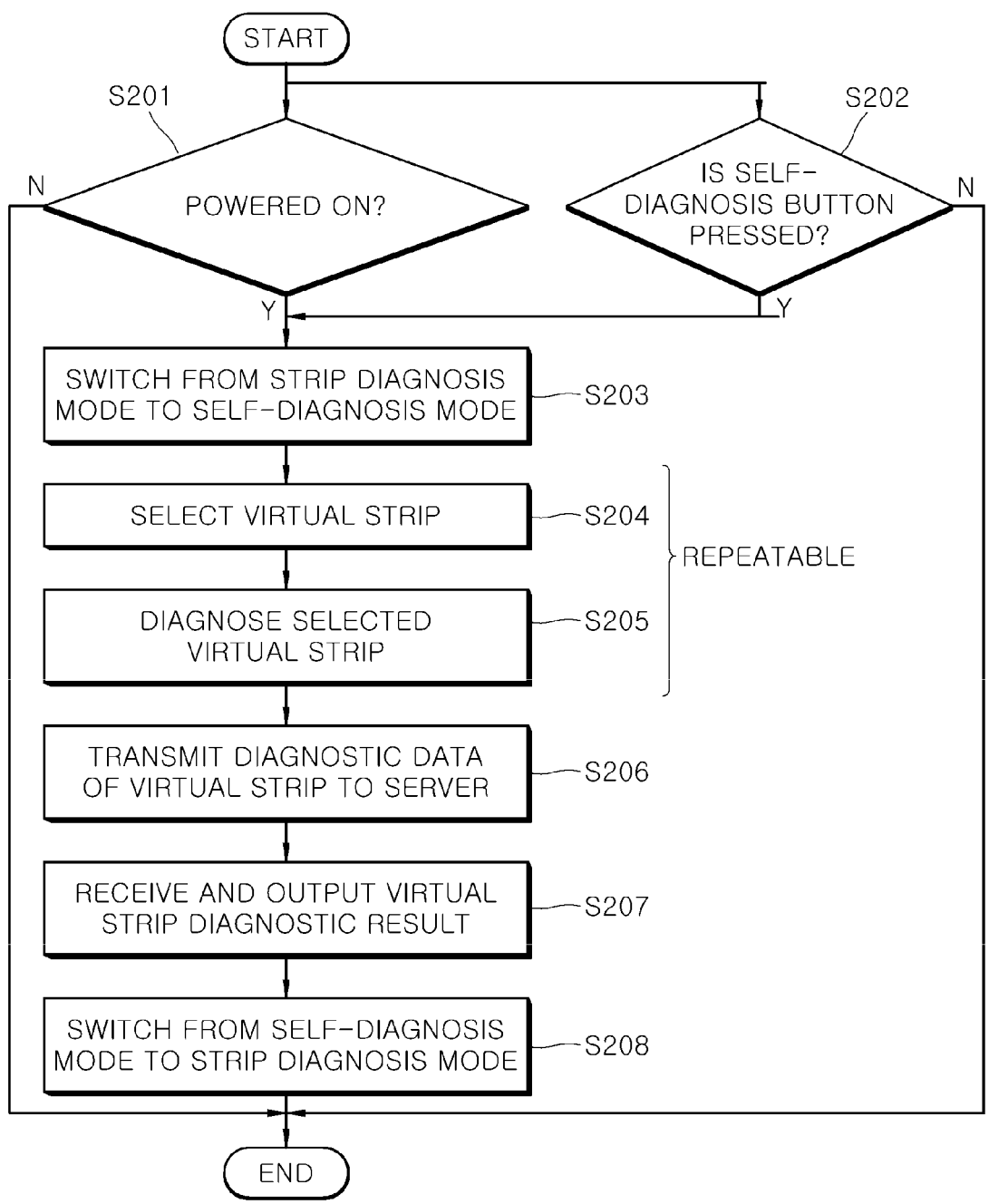
FIG. 6 is a flowchart for describing the self-diagnosis method for a health tester of FIG. 5.

FIG. 4 is a flowchart illustrating a self-diagnosis method for a health tester according to a first embodiment of the present invention, FIG. 5 is an exemplary diagram for describing a self-diagnosis method for a health tester according to a second embodiment of the present invention, and FIG. 6 is a flowchart for describing the self-diagnosis method for a health tester of FIG. 5.

Referring to FIG. 4, when a health tester is powered on (YES in S101) or when a specific button (e.g., a self-diagnosis button) provided on the health tester is pressed (YES in S102), the controller 150 may change a switch (i.e., a switch for selecting an actual strip or a virtual strip) from an actual strip diagnosis mode (i.e., a mode for self-diagnosing blood using an actual strip) to a self-diagnosis mode (i.e., a mode for self-diagnosing a performance or failure of the health tester itself) (S103).

In this case, although not illustrated, besides the two cases (e.g., power on and specific button input), when an actual strip is inserted into the health tester, the controller 150 may change the switch from the actual strip diagnosis mode to the self-diagnosis mode.

When the self-diagnosis mode is activated, the controller 150 sequentially or simultaneously selects one or more of the virtual strips 121 to 120 from the virtual strip unit 120 according to a predetermined program (S104), and diagnoses (or measures) the selected one or more virtual strips (S105).

In this case, the selection and diagnosis operations (S104 and S105) of the virtual strips may be performed a number of times according to a combination set in advance.

When the diagnosis of the selected one or more virtual strips is completed, the controller 150 outputs a diagnostic result about a status (or the occurrence of a failure) of the health tester on the basis of the diagnostic data (S106).

At this time, when the status of the health tester does not meet a reference condition or a failure occurs according to the diagnostic result, the controller 150 may set (or control) the health tester to be unavailable for use or measurement.

When the diagnostic result is output as described above, the controller 150 switches from the self-diagnosis mode (i.e., the mode for self-diagnosing the performance or failure of the health tester) back to the actual strip diagnosis mode (i.e., the mode for diagnosing blood using an actual strip) (S107).

Meanwhile, referring to FIG. 5, a self-diagnosis apparatus 100 for a health tester according to the present embodiment may transmit data obtained by diagnosing virtual strips in the self-diagnosis mode to a server 200 (e.g., a cloud server, a status diagnosis server, etc.) through the Internet, and the server 200 may transmit a result of diagnosing status (or the occurrence of a failure) of the health tester on the basis of diagnostic data of the virtual strip received through the Internet, thereby enabling the health tester to output the diagnostic result.

Accordingly, the self-diagnosis apparatus 100 for a health tester according to the present embodiment may further include a communicator (not shown) for communication with the server 200.

FIG. 6 is a flowchart for describing the self-diagnosis method for a health tester of FIG. 5. The self-diagnosis method for a health tester according to the second embodiment of the present invention described with reference to FIG. 5 differs from the self-diagnosis method for a health tester according to the first embodiment of the present invention in operations S206 and S207.

That is, referring to FIG. 6, when a health tester is powered on (YES in S201), when a specific button (e.g., a self-diagnosis button) provided on the health tester is pressed (YES in S202), or when an actual strip is inserted into the health tester (not shown), the controller 150 changes from the actual strip diagnosis mode to the self-diagnosis mode (S203), sequentially or simultaneously selects one or more of the strips 121 to 123 from the virtual strip unit 120 (S204), and diagnoses (or measures) the selected one or more virtual strips (S205).

Accordingly, when the diagnosis of the one or more virtual strips selected in the self-diagnosis mode is completed, the controller 150 transmits data obtained by diagnosing the virtual strips to the server 200 (e.g., a cloud server, a status diagnosis server, etc.) through the Internet (S206), and receives and outputs a diagnostic result from the server 200 which diagnoses status (or the occurrence of a failure) of the health tester on the basis of diagnostic data of the virtual strips transmitted through the Internet (S207).

When the diagnostic result is output, the controller 150 changes from the self-diagnosis mode (i.e., the mode for self-diagnosing a performance or failure of the health tester) back to the actual strip diagnosis mode (i.e., the mode for diagnosing blood using an actual strip) (S208).

When the status of the health tester is diagnosed through the server as described above, resources of the health tester itself can be reduced and a program upgrade for a new diagnostic item or a diagnostic method can be easily performed in the server 200 itself. In addition, according to the present embodiment, the performance or failure of the health tester is self-diagnosed regularly, thereby ensuring reliability of blood diagnosis data by the actual strip.

According to one aspect of the present invention, a health tester is enabled to autonomously self-diagnose a performance or failure thereof, thereby ensuring reliability of diagnostic data.

While the present invention has been particularly shown and described with reference to exemplary embodiments thereof, it should be understood by those of ordinary skill in the art that various changes in form and details may be made therein without departing from the spirit and scope of the present invention as defined by the following claims.

What is claimed is:

1. A self-diagnosis apparatus for a health tester which is configured to display diagnostic information of a user obtained using a strip and have a communication function capable of transmitting the diagnostic information to an external device, the self-diagnosis apparatus comprising:
   a virtual strip unit mounted inside of the health tester and configured to include one or more virtual strips in which predetermined specific data is measured;
   a virtual strip selector configured to select at least one virtual strip from the one or more virtual strips through switching; and
   a diagnosis and determination unit configured to connect the selected at least one virtual strip selected by the virtual strip selector to a measurer and diagnose a status or an occurrence of a failure of the health tester on the basis of diagnostic data of the virtual strip measured by the measurer when the status or the occurrence of a failure of the health tester is self-diagnosed,
   wherein the virtual strip includes a transistor operating as a switch, wherein, when a control signal output from the controller is applied to a gate of the transistor, a source and a drain are connected to each other and an RLC equivalent circuit is connected to the measurer.

2. The self-diagnosis apparatus of claim 1, wherein the diagnosis and determination unit sequentially connects all of the virtual strips of the virtual strip unit to the measurer, or simultaneously selects one or more of the virtual strips and connects the selected virtual strips to the measurer to self-diagnose the status or the occurrence of a failure of the health tester.

3. The self-diagnosis apparatus of claim 1, wherein the diagnosis and determination unit performs at least one of a current or voltage analysis, an impedance analysis, an impulse analysis, and a spectrum analysis to diagnose the status or the occurrence of a failure of the health tester.

4. The self-diagnosis apparatus of claim 1, wherein the one or more virtual strips are each configured as a strip equivalent circuit in which the predetermined specific data is measured.

5. The self-diagnosis apparatus of claim 1, wherein the virtual strip selector measures and diagnoses an actual strip at a time of actual blood diagnosis and measures and diagnoses the virtual strip at a time of self-diagnosis under control of the diagnosis and determination unit.

6. The self-diagnosis apparatus of claim 1, wherein the virtual strip selector and the virtual strip unit are implemented as one component or module, and the virtual strip unit is implemented to be detachable.

7. The self-diagnosis apparatus of claim 1, wherein the diagnosis and determination unit compares the diagnostic data of the at least one virtual strip and diagnostic data for each of the virtual strips stored in advance in an internal memory and diagnoses the status of the health tester according to whether the two pieces of data match each other within an error range.

8. The self-diagnosis apparatus of claim 1, wherein the virtual strip is implemented as an equivalent electronic circuit corresponding to a function of an actual strip on which any blood is collected.

9. The self-diagnosis apparatus of claim 1, wherein the virtual strip is implemented such that a value of the RLC equivalent circuit is set differently according to a type of virtual strips for self-diagnosis of different operations of the health tester, and accordingly, the measurer measures different diagnostic data depending on the type of virtual strip.

10. The self-diagnosis apparatus of claim 1, wherein, when the status of the health tester does not meet a reference condition or a failure occurs, the diagnosis and determination unit displays the status and sets the health tester to be unavailable for use or measurement.

* * * * *